(12) United States Patent
Vekselman

(10) Patent No.: US 12,013,238 B2
(45) Date of Patent: Jun. 18, 2024

(54) SYSTEMS, DEVICES, AND METHODS FOR BEAM MISALIGNMENT DETECTION

(71) Applicant: TAE TECHNOLOGIES, INC., Foothill Ranch, CA (US)

(72) Inventor: Vladislav Vekselman, Lake Forest, CA (US)

(73) Assignee: TAE TECHNOLOGIES, INC., Foothill Ranch, CA (US)

( * ) Notice: Subject to any disclaimer, the term of this patent is extended or adjusted under 35 U.S.C. 154(b) by 381 days.

(21) Appl. No.: 17/411,857

(22) Filed: Aug. 25, 2021

(65) Prior Publication Data

US 2022/0065611 A1 Mar. 3, 2022

Related U.S. Application Data

(60) Provisional application No. 63/071,185, filed on Aug. 27, 2020, provisional application No. 63/070,799, filed on Aug. 26, 2020.

(51) Int. Cl.
| | |
|---|---|
| *G01B 7/31* | (2006.01) |
| *A61N 5/10* | (2006.01) |
| *H05H 3/06* | (2006.01) |
| *H05H 7/08* | (2006.01) |

(52) U.S. Cl.
CPC .............. *G01B 7/31* (2013.01); *H05H 3/06* (2013.01); *H05H 7/08* (2013.01); *A61N 5/1048* (2013.01); *A61N 2005/109* (2013.01); *H05H 2277/11* (2013.01)

(58) Field of Classification Search
CPC ... G01B 7/31; H05H 3/06; H05H 7/08; H05H 2277/11; A61N 5/1048; A61N 2005/109; A61N 5/1075; G01R 19/0061; G01R 15/20; G01R 19/16571; G01R 19/16576; G01R 19/1659

See application file for complete search history.

(56) References Cited

U.S. PATENT DOCUMENTS

| | | | | |
|---|---|---|---|---|
| 3,713,967 | A | * | 1/1973 | Hamilton ............... G21K 1/14 976/DIG. 437 |
| 4,480,185 | A | * | 10/1984 | Hashimoto ............ H05H 1/22 976/DIG. 437 |
| 4,583,025 | A | * | 4/1986 | Adler .................... H01J 25/02 315/5 |
| 11,817,292 | B2 | * | 11/2023 | Breuer ................ H01J 37/1472 |

(Continued)

FOREIGN PATENT DOCUMENTS

| | | |
|---|---|---|
| JP | S63 141298 A | 6/1988 |
| JP | H03 261100 A | 11/1991 |
| WO | WO 2022/046936 A2 | 3/2022 |

OTHER PUBLICATIONS

PCT/US2021/047602 International Search Report and Written Opinion dated Feb. 24, 2022.

(Continued)

*Primary Examiner* — David A Vanore
(74) *Attorney, Agent, or Firm* — ALSTON & BIRD LLP

(57) ABSTRACT

Embodiments of systems, devices, and methods relating to a beam system. An example method of detecting beam misalignment a beam system includes detecting beam misalignment in an injector system of the beam system. The example method further includes detecting beam misalignment in an accelerator system of the beam system.

22 Claims, 10 Drawing Sheets

(56) References Cited

U.S. PATENT DOCUMENTS

| | | | |
|---|---|---|---|
| 2010/0141183 A1* | 6/2010 | Balakin | H05H 13/04 |
| | | | 315/503 |
| 2011/0186746 A1 | 8/2011 | Drees et al. | |
| 2012/0181443 A1* | 7/2012 | Riordon | H01J 37/3171 |
| | | | 250/395 |
| 2013/0068963 A1 | 3/2013 | Kireeff | |
| 2016/0217973 A1* | 7/2016 | Ishida | H01J 37/244 |
| 2018/0206323 A1* | 7/2018 | Kobernik | H05B 31/26 |
| 2022/0065611 A1* | 3/2022 | Vekselman | H05H 7/08 |
| 2023/0199935 A1* | 6/2023 | Miyaoka | H05H 7/04 |
| | | | 315/505 |

OTHER PUBLICATIONS

Peters, et al., "Beam Diagnostics for the Heavy Ion Cancer Therapy Facility," AIP Conference Proceedings, American Institute of Physics, New York, US, No. 546, pp. 519-526, (May 8, 2000).

* cited by examiner

SYSTEMS, DEVICES, AND METHODS FOR BEAM MISALIGNMENT DETECTION

CROSS-REFERENCE TO RELATED APPLICATIONS

The present application claims priority to U.S. Provisional Application Ser. No. 63/070,799, titled "SYSTEMS, DEVICES, AND METHODS FOR BEAM MISALIGNMENT DETECTION," filed Aug. 26, 2020, and to U.S. Provisional Application Ser. No. 63/071,185, titled "SYSTEMS, DEVICES, AND METHODS FOR BEAM MISALIGNMENT DETECTION," filed Aug. 27, 2020, the contents of both of which are incorporated herein by reference in their entirety for all purposes.

FIELD

The subject matter described herein relates generally to systems, devices, and methods of detecting, adjusting, and safely discontinuing misaligned beams in accelerator systems.

BACKGROUND

Boron neutron capture therapy (BNCT) is a modality of treatment of a variety of types of cancer, including some of the most difficult types. BNCT is a technique that selectively aims to treat tumor cells while sparing the normal cells using a boron compound. A substance that contains boron is injected into a blood vessel, and the boron collects in tumor cells. The patient then receives radiation therapy with neutrons (e.g., in the form of a neutron beam). The neutrons react with the boron to kill the tumor cells while reducing harm to surrounding normal cells. Prolonged clinical research has proven that a beam of neutrons with an energy spectrum within 3-30 kiloelectronvolts (keV) is preferable to achieve a more efficient cancer treatment while decreasing a radiation load on a patient. This energy spectrum or range is frequently referred to as epithermal.

Most conventional methods for the generation of epithermal neutrons (e.g., epithermal neutron beams) are based on nuclear reactions of protons with either beryllium or lithium (e.g., a beryllium target or a lithium target).

For solutions based on electrostatic accelerators, beam diagnostics is an intrinsic part of the charged particle beamline design. A critical task in beam transport is to ensure that the beam is correctly positioned inside the beamline (e.g., there is no direct beam interaction with beamline components and walls). Any impact of placement or use of such beam diagnostics can be proportional to the beam energy as the beam destructive power goes up with beam energy. This is especially true for the transport of direct current (DC) beams where irreversible damage to the beamline components as well as patients receiving treatment based on the beams can be created at millisecond time scale. Therefore, continuous monitoring of the beam position is a key to success with the beam transport in accelerator-based solutions as is the ability to quickly discontinue or adjust beams that have been detected as being misaligned.

For these and other reasons, a need exists for improved, efficient, and compact systems, devices, and methods that safely monitor and enable discontinuation of misaligned beams transported in accelerator-based solutions.

SUMMARY

Example embodiments of systems, devices, and methods are described herein for beam misalignment detection in injector systems of neutron beam systems as well as accelerator systems of neutron beam systems. Example embodiments relate to detection of beam misalignment in a beam system.

In various embodiments, beam misalignment can be detected in a beam injector or injector system of a beam system based on obtaining a current measurement from a magnetic element of the beam injector or obtaining a voltage measurement of a biased component of the beam injector. A beam can be determined to be misaligned when the current measurement deviates from nominal conditions or when the voltage measurement deviates from nominal conditions.

In various embodiments, beam misalignment can be detected in an accelerator system of a beam system based on obtaining input beam current and output beam current of the accelerator system as well as various parameters associated with a charge exchange device of the accelerator system to evaluate beam losses. A beam can be determined to be misaligned when detected beam losses exceed a beam loss threshold.

Other systems, devices, methods, features and advantages of the subject matter described herein will be or will become apparent to one with skill in the art upon examination of the following figures and detailed description. It is intended that all such additional systems, methods, features and advantages be included within this description, be within the scope of the subject matter described herein and be protected by the accompanying claims. In no way should the features of the example embodiments be construed as limiting the appended claims, absent express recitation of those features in the claims.

BRIEF DESCRIPTION OF FIGURES

The details of the subject matter set forth herein, both as to its structure and operation, can be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes can be illustrated schematically rather than literally or precisely.

DETAILED DESCRIPTION

Figure 1A:
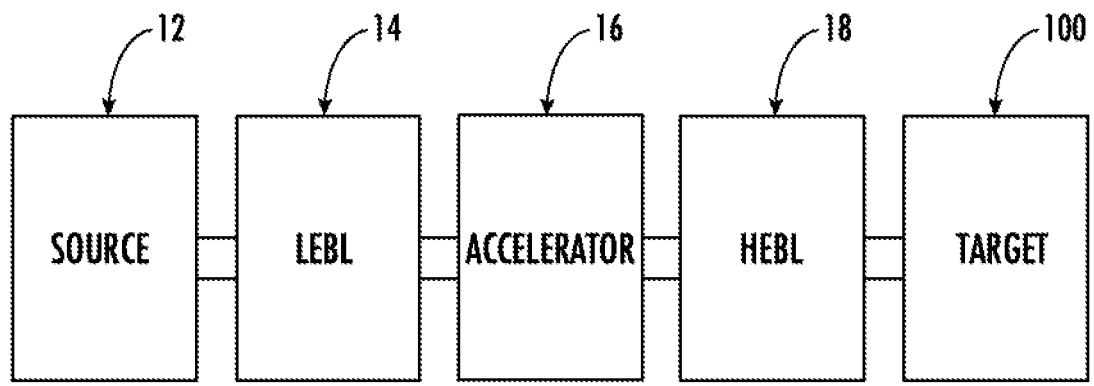
FIG. 1A is a schematic diagram of an example embodiment of a neutron beam system for use with embodiments of the present disclosure.

Before the present subject matter is described in detail, it is to be understood that this disclosure is not limited to the particular embodiments described, as such can, of course, vary. It is also to be understood that the terminology used herein is for the purpose of describing particular embodiments only, and is not intended to be limiting, since the scope of the present disclosure will be limited only by the appended claims.

The term "particle" is used broadly herein and, unless otherwise limited, can be used to describe an electron, a proton (or H+ ion), or a neutron, as well as a species having more than one electron, proton, and/or neutron (e.g., other ions, atoms, and molecules).

Boron neutron capture therapy (BNCT) involves deploying a high energy (e.g., 2-3 Megaelectronvolts (MeV)) and high current (e.g., up to 20 milliamps (mA)) DC proton beam for the cancer treatment. Such a powerful beam can result in the possible creation of harmful events triggered by beam misalignment, interruption, failure of beamline components, or the development of beam instabilities. For example, direct interaction of the beam with a beamline wall can lead to irreversible damage within milliseconds.

Embodiments of the present disclosure enable monitoring and prevention of such undesired events during system operation through the use of beam diagnostics and a control system configured to employ methods for detection of beam misalignment and adjustment or discontinuing of a misaligned beam.

Beam transport simulations are typically performed to determine "safe corridors" for various beam characteristics, including but not limited to: deviation of the beam from the optimal pathway in space and phase coordinates, beam size limitations, beam energy variation, and the like. These simulations are complicated and sometimes of insufficient accuracy amid uncertainty in initial conditions and intrinsic inaccuracy of applied methods, but the simulations can be benchmarked with experiments to bring a confidence in the results. The benchmarking of simulation results depends on accurate beam characterization and monitoring during machine or system commissioning and operation achievable through non-invasive diagnostic tools.

Non-invasive measurements of the beam characteristics are challenging to perform, especially for high power DC beams (where invasive diagnostics are inappropriate). Considering space limitations and other restrictions acting along the beamline, the actual set of beam diagnostics can only be able to deliver partial information about the beam. Example embodiments of the present disclosure overcome such spot-like coverage of the beam by enabling a reliable interlock system and methods to certify the safety and reliability of the beam transport. Embodiments described herein enable timely and reliable interpretation of the relevant signals from beam diagnostics followed by initiation of beam discontinuation if needed.

Embodiments described herein can include dedicated non-invasive or minimally invasive beam diagnostics that result in minimal beam perturbation or disturbance during measurements. That is, beam measurements using interceptive or invasive beam diagnostics affect beam characteristics via beam-probe interaction. For example, the beam space and phase profiles are commonly affected beam characteristics as well as beam energy. Therefore, interceptive or invasive beam diagnostics are generally only suitable for use during machine commissioning phase or during the machine maintenance or service.

Embodiments described herein can further enable redundant measurements of various beam characteristics or parameters. Redundancy can be achieved, in certain example embodiments, by way of comparing two or more signals from different measurements in order to determine a resulting signal. Redundancy can further be achieved, in certain example embodiments, by way of determining whether different measurements are indicative of beam misalignment based upon various dynamic or fixed calculations. Redundancy can be achieved herein through the use of hardware, software, or a combination of both.

Time-resolved measurements of the beam parameters can be affected by different phenomena which can be accounted for based upon an accuracy of a measurement. For example, the collection of beam particles on an electrical probe surface, enabling estimating of the beam current, is accompanied by a phenomenon known as secondary particle emission. Secondary particle emission commonly results in an incorrect estimation of beam current, and for a negative ion beam the beam current can be underestimated due to such emitted secondary electrons. Biasing of the electrical probe and/or application of an external magnetic field of specific configuration can diminish the effect of the secondary particle emission. However, other charged particles can be attracted by the electrical probe from nearby generated plasma thus limiting the accuracy of electrical probe generated signals.

As beam particulates can be exclusively generated by an ion source (e.g., 12), beam current preferably does not increase while the beam propagates downstream through a beam system (e.g., 10). Such a condition can be employed herein to detect incorrect readings of beam diagnostics. For example, $I_i \geq I_j$ for $j \geq i$, where i, j are indexes of beam diagnostics in the beamline (e.g., beam system 10) incremented from the ion source (e.g., 12), and $I_i$ (or $I_j$) is a measured beam parameter. For example, the beam total current measured at an exit of the ion source (e.g., 12) should not be smaller than the beam total current injected into the accelerator system (e.g., 16), which is measured at the entrance of the accelerator system (e.g., 16).

Example embodiments of systems, devices, and methods described herein can include a pre-accelerator system for use with a particle accelerator. Particle accelerators are a common example, and the embodiments described herein can be used with any type of particle accelerator or in any particle accelerator application involving production of a charged particle beam at specified energies for supply to the particle accelerator. Embodiments of the present pre-accelerator system or ion beam injector are suited to provide a negative particle beam to a tandem accelerator, but this is just an example type of accelerator. The pre-accelerator embodiments described herein can be implemented in: particle accelerators used as scientific tools, such as for nuclear physics research; particle accelerators used in industrial or manufacturing processes, such as the manufacturing of semiconductor chips; accelerators for the alteration of material properties (such as surface treatment); particle accelerators for the irradiation of food; and particle accelerators for pathogen destruction in medical sterilization. The embodiments can also be used in imaging applications, such as cargo or container inspection. And by way of another non-exhaustive example, the embodiments can be used in particle accelerators for medical applications, such as medical diagnostic systems, medical imaging systems, or radiation therapy systems.

One such radiation therapy system is a BNCT system. For ease of description, many embodiments described herein will be done so in the context of a neutron beam system for use in BNCT, although the embodiments are not limited to just neutron beams nor BNCT applications. Embodiments of the present disclosure enable configuration of an accelerator system (also referred to herein as a pre-accelerator system) for generating a proton beam with parameters suitable for sources of neutrons for BNCT with neutron generating targets, such as lithium (Li) or beryllium (Be).

For efficient generation of epithermal neutrons on a lithium target, a beam of protons with energies of 1.9-3.0 MeV can be desirable. The formation of a neutron beam with a preferable flux density for reasonably short treatment time, in such applications, can also involve a proton beam current above 5 mA. In order to employ tandem accelerator systems in such applications, a source of negative ions of hydrogen can be preferred.

Embodiments of the present disclosure can be useful for any type of electrostatic accelerators of negative ions with the beam current above a few milliamps. The embodiments disclosed herein can have any additional elements including ion optics and beam diagnostics before, within, or after the pre-accelerator system, as required by a particular application.

Embodiments of the present disclosure can be used with a neutron beam system (NBS) that provides a continuous or modulated proton beam. The proton beam can have a wide range of energies and currents. For example, in some embodiments the proton beam has a particle energy in the range of 1.9-3.0 MeV with a beam current of 5-15 mA. In other embodiments, the proton beam has energies and/or currents outside these ranges. The beam can be directed to a lithium target to generate a neutron beam, or the NBS can be used with targets having other materials for neutron generation, such as beryllium instead of lithium.

In some embodiments, the ion source generates a beam of negative ions of hydrogen with a current up to 15 mA (or higher). The beam particles can be accelerated in the ion source to an energy of 30 keV (or higher). The ion source can be connected to the pre-accelerator system (with one or more intervening components), which provides additional acceleration of negative ion beam particles to the energy of 120-150 keV (or higher). The beam can be also focused in the pre-accelerator system with a focal length correspondent to the distance to the input aperture of the tandem accelerator input chamber, e.g., a distance of less than one meter (m). The pre-accelerator system can include an electrostatic lens (e.g., an einzel lens), a pre-accelerator device (e.g., a pre-accelerator tube having multiple terminals), and/or a magnetic element (e.g., one or more solenoids) for shaping and accelerating the ion beam to higher energies prior to entering the tandem accelerator.

The electrostatic lens of the pre-accelerator system can be positioned between the ion source and the pre-accelerator tube such that the electrostatic lens is downstream from a ground lens of the ion source. The electrostatic lens can reduce divergence of the ion beam from the ion source, and can also divert and collect ionized backflow particles.

The magnetic element (or magnetic focusing device) of the pre-accelerator system can be positioned between the pre-accelerator tube and the tandem accelerator, and can fine tune the beam toward the focal spot. The magnetic element can be, for example, a solenoid.

Example embodiments of systems, devices, and methods described herein also facilitate fast beam position monitoring for detection of beam misalignment in a beamline of a beam system 10. In certain example embodiments, the beam position monitor (BPM) can include multiple electrodes extending into the interior of the beamline of the neutron beam system (NB S). In these embodiments, the beam position monitor (BPM) can operate by collection of the beam halo current by the electrodes. The electrodes can be galvanically isolated from a wall of the BPM and biased using an external power supply. Biasing relative to the BPM wall can reduce contribution of secondary electron emission (SEE) current to the signal and can increase the beam halo current collected from the beam generated plasma.

In example embodiments, the beam position monitor (BPM) is configured to signal or indicate to a control system when a beam advancing through the beam line is off axis.

The beam position monitor (BPM) can include a detection sensitivity level associated with reducing or eliminating beam-induced damage to beamline components while minimizing disturbance to the beam advancing through the beam line. That is, a minimal amount of a beam current of the beam passing through the component of the beam line can be reduced as a result of current collection by the electrodes. Example embodiments of the BPM can advantageously operate with direct current (DC) beams, have millisecond (or faster) response time, and/or accept beam powers of 2.5 MeV (and higher) per nuclei.

In some example embodiments, the BPM can be part of a beam system configured for producing a neutron beam from an ion beam. The beam system can include an LEBL, serving as an ion beam injector system, a high voltage (HV) tandem accelerator coupled to the ion beam injector system, and an HEBL extending from the tandem accelerator to a neutron target assembly housing a neutron-producing target. In these example embodiments, the ion beam injector can include an ion source, beam optics incorporated into a low-energy beamline extending from the ion source, a pre-accelerator tube, beam diagnostics and a pumping chamber coupled to the tandem accelerator. The ion source can generate charged particles in the plasma volume which can be extracted, accelerated, conditioned and eventually used to produce neutrons when delivered to the neutron producing target. Such improved, efficient, and compact systems, devices, and methods that monitor the beam position enable preservation of neutron beam system equipment while maintaining operative efficacy.

FIG. 1A is a schematic diagram of an example embodiment of a beam system 10 for use with embodiments of the present disclosure. Here, beam system 10 includes a source 12, a low-energy beamline (LEBL) 14, an accelerator 16 coupled to the low-energy beamline (LEBL) 14, and a high-energy beamline (HEBL) 18 extending from the accelerator 16 to a target 100. LEBL 14 is configured to transport a beam from source 12 to an input of accelerator 16, which in turn is configured to produce a beam by accelerating the beam transported by LEBL 14. HEBL 18 transfers the beam from an output of accelerator 16 to target 100. Target 100 can be a structure configured to produce a desired result in response to the stimulus applied by the incident beam, or can modify the nature of the beam. Target 100 can be a component of system 10 or can be a workpiece that is conditioned or manufactured, at least in part, by system 10.

Figure 1B:
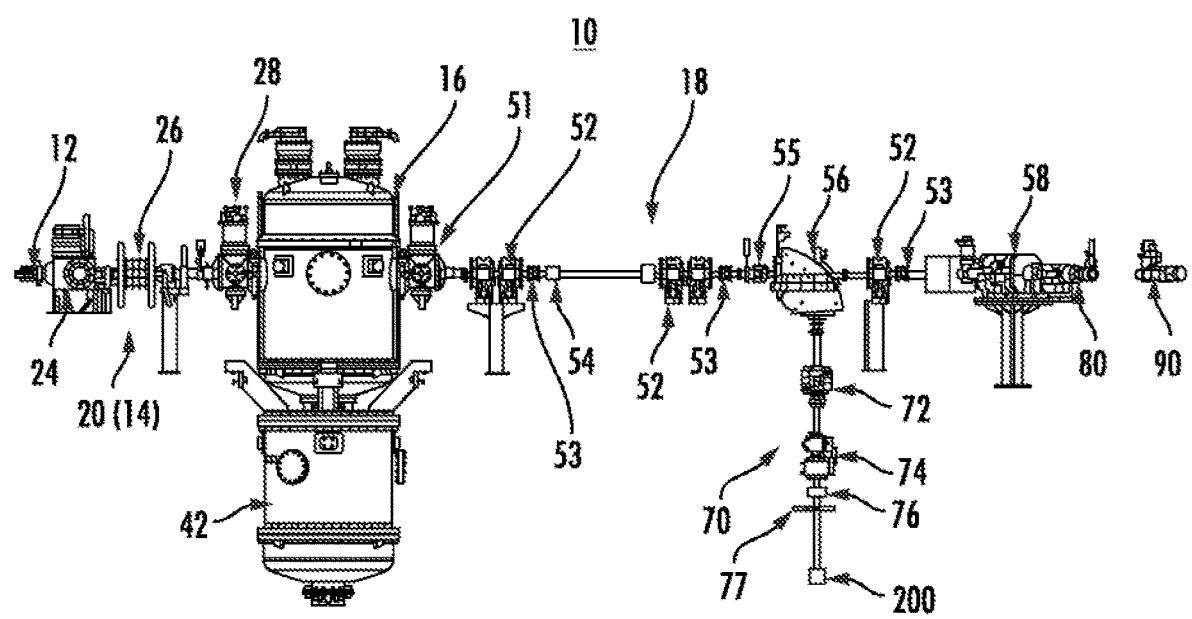
FIG. 1B is a schematic diagram of an example embodiment of a neutron beam system for use in boron neutron capture therapy (BNCT).

FIG. 1B is a schematic diagram illustrating another example embodiment of a neutron beam system 10 for use in boron neutron capture therapy (BNCT). Here, source 12 is an ion source and accelerator 16 is a tandem accelerator.

Neutron beam system 10 includes a pre-accelerator system 20, serving as a charged particle beam injector, high voltage (HV) tandem accelerator 16 coupled to pre-accelerator system 20, and HEBL 18 extending from tandem accelerator 16 to a neutron target assembly 200 housing target 100 (not shown). In this embodiment target 100 is configured to generate neutrons in response to impact by protons of a sufficient energy, and can be referred to as a neutron generation target. Neutron beam system 10 as well as pre-accelerator system 20 can also be used for other applications such as those other examples described herein, and is not limited to BNCT.

Pre-accelerator system 20 is configured to transport the ion beam from ion source 12 to the input (e.g., an input aperture) of tandem accelerator 16, and thus also acts as LEBL 14. Tandem accelerator 16, which is powered by a high voltage power supply 42 coupled thereto, can produce a proton beam with an energy generally equal to twice the voltage applied to the accelerating electrodes positioned within accelerator 16. The energy level of the proton beam can be achieved by accelerating the beam of negative hydrogen ions from the input of accelerator 16 to the innermost high-potential electrode, stripping two electrons from each ion, and then accelerating the resulting protons downstream by the same applied voltage.

HEBL 18 can transfer the proton beam from the output of accelerator 16 to the target within neutron target assembly 200 positioned at the end of a branch 70 of the beamline extending into a patient treatment room. System 10 can be configured to direct the proton beam to any number of one or more targets and associated treatment areas. In this embodiment, the HEBL 18 includes three branches 70, 80 and 90 that can extend into three different patient treatment rooms, where each branch can terminate in a target assembly 200 and downstream beam shaping apparatus (not shown). HEBL 18 can include a pump chamber 51, quadrupole magnets 52 and 72 to prevent de-focusing of the beam, dipole or bending magnets 56 and 58 to steer the beam into treatment rooms, beam correctors 53, diagnostics such as current monitors 54 and 76, a fast beam position monitor 55 section, and a scanning magnet 74.

The design of HEBL 18 depends on the configuration of the treatment facility (e.g., a single-story configuration of a treatment facility, a two-story configuration of a treatment facility, and the like). The beam can be delivered to target assembly (e.g., positioned near a treatment room) 200 with the use of bending magnet 56. Quadrupole magnets 72 can be included to then focus the beam to a certain size at the target. Then, the beam passes one or more scanning magnets 74, which provides lateral movement of the beam onto the target surface in a desired pattern (e.g., spiral, curved, stepped in rows and columns, combinations thereof, and others). The beam lateral movement can help achieve smooth and even time-averaged distribution of the proton beam on the lithium target, preventing overheating and making the neutron generation as uniform as possible within the lithium layer.

After entering scanning magnets 74, the beam can be delivered into a current monitor 76, which measures beam current. Target assembly 200 can be physically separated from the HEBL volume with a gate valve 77. The main function of the gate valve is separation of the vacuum volume of the beamline from the target while loading the target and/or exchanging a used target for a new one. In embodiments, the beam may not be bent by 90 degrees by a bending magnet 56, it rather goes straight to the right of FIG. 1B, then enters quadrupole magnets 52, which are located in the horizontal beamline. The beam could be subsequently bent by another bending magnet 58 to a needed angle, depending on the building and room configuration. Otherwise, bending magnet 58 could be replaced with a Y-shaped magnet in order to split the beamline into two directions for two different treatment rooms located on the same floor.

Figure 2:
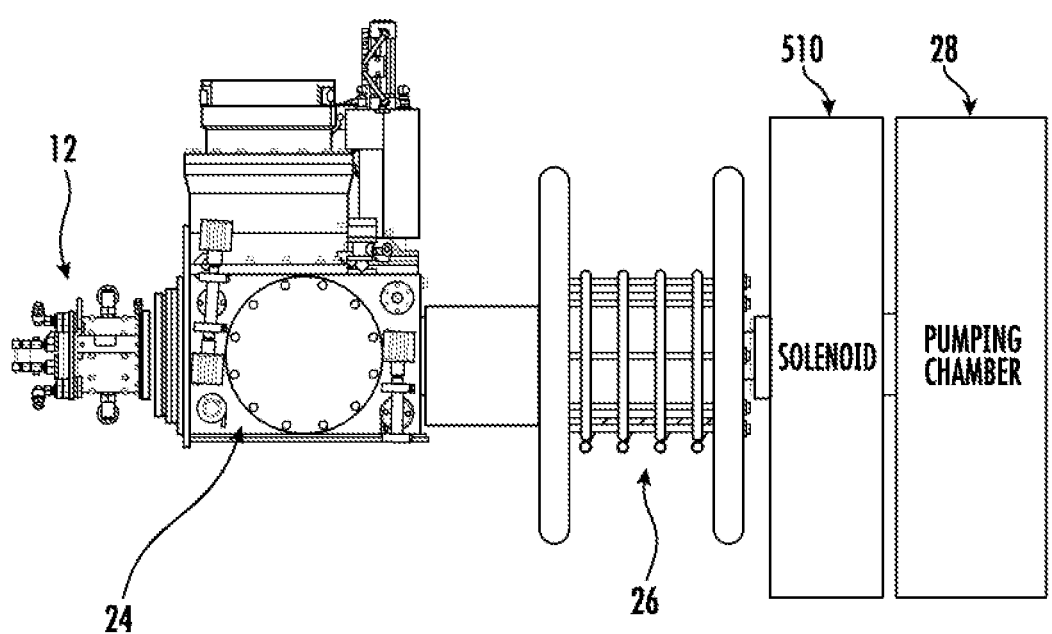
FIG. 2 illustrates an example pre-accelerator system or ion beam injector for use with embodiments of the present disclosure.

FIG. 2 illustrates an example of a pre-accelerator system or ion beam injector for use with embodiments of the present disclosure. In this example, pre-accelerator system 20 (e.g., LEBL 14) includes an einzel lens 30 (not shown), a pre-accelerator tube 26, and a solenoid 510, and is configured to accelerate a negative ion beam injected from ion source 12. The pre-accelerator system 20 is configured to provide acceleration of the beam particles to the energies required for tandem accelerator 16, and to provide overall convergence of the negative ion beam to match input aperture area at an input aperture or entrance of the tandem accelerator 16. The pre-accelerator system 20 is further configured to minimize or defocus backflow as it passes from the tandem accelerator 16 through the pre-accelerator system in order to reduce the possibility of damage to ion source 12 and/or the backflow reaching the filaments of the ion source.

In embodiments, the ion source 12 can be configured to provide a negative ion beam upstream of the einzel lens 30, and the negative ion beam continues to pass through pre-accelerator tube 26 and a magnetic focusing device (e.g., solenoid) 510. The solenoid 510 can be positioned between the pre-accelerator tube 26 and the tandem accelerator 16 and is electrically couplable with a power supply. The negative ion beam passes through the solenoid 510 to the tandem accelerator 16.

Pre-accelerator system 20 can also include an ion source vacuum box 24 for removing gas, and a pump chamber 28, which, with pre-accelerator tube 26 as well as the other elements described above are part of a relatively low energy beamline leading to the tandem accelerator 16. The ion source vacuum box 24, within which the einzel lens 30 can be positioned, extends from the ion source 12. The pre-accelerator tube 26 can be coupled to the ion source vacuum box 24 and to solenoid 510. A vacuum pump chamber 28 for removing gas can be coupled to the solenoid 510 and the tandem accelerator 16. The ion source 12 serves as a source of charged particles which can be accelerated, conditioned and eventually used to produce neutrons when delivered to a neutron producing target. The example embodiments will be described herein with reference to an ion source producing a negative hydrogen ion beam, although embodiments are not limited to such, and other positive or negative particles can be produced by the source.

The pre-accelerator system 20 can have zero, one, or multiple magnetic elements for purposes such as focusing and/or adjusting alignment of the beam. For example, any such magnetic elements can be used to match the beam to the beamline axis and the acceptance angle of the tandem accelerator 16. The ion vacuum box 24 can have ion optics positioned therein.

There are generally two types of negative ion sources 12, which differ by the mechanism of generation of negative ions: the surface type and the volume type. The surface type generally requires the presence of cesium (Cs) on specific internal surfaces. The volume type relies on formation of negative ions in the volume of a high current discharge plasma. While both types of ion sources can deliver the desired negative ion current for applications related to tandem accelerators, surface type negative ion sources are undesirable for modulation. That is, for modulation of a negative ion beam in embodiments described herein, negative ion sources of the volume type (e.g., without employing cesium (Cs)) are preferred.

An injector system (e.g., pre-accelerator system 20; e.g., LEBL 14) can enable generation of beam particles, beam formation, beam transport and beam matching to the accelerator system (e.g., 16). The beam energy in the injector system (e.g., pre-accelerator system 20; e.g., LEBL 14) can be relatively small (e.g., 50-200 kiloelectronvolts (keV)), which can decrease the probability of irreversible injector system damage upon beam misalignment (e.g., and direct beam-wall interaction). However, misalignment of the beam in an injector system (e.g., 20, 14) can lead to serious consequences related to beam transport downstream the injector system (e.g., in the accelerator 16 and downstream in the HEBL 18). A misaligned (e.g., mismatched) beam is likely a root cause of machine performance degradation or even malfunctioning and damage.

In embodiments, beam misalignment in an injector system (e.g., pre-accelerator system 20; e.g., LEBL 14) can be detected based on obtaining current measurements from one or more magnetic elements of the beam injector system (e.g., 20, 14). That is, performance of magnetic-type ion optics, steering magnet shifters, magnetic elements, or a solenoid can be monitored via time-resolved current magnitude readings. Deviations of the current measurements obtained from these components from nominal conditions, or from an alignment current range, can signal that the beam passing through the injector system is misaligned.

In embodiments, beam misalignment in an injector system (e.g., pre-accelerator system 20; e.g., LEBL 14) can be detected by obtaining voltage measurements from at least one biased component of the beam injector system (e.g., 20, 14). That is, performance of one or more biased components such as an ion source (e.g., 12), a pre-accelerator tube (e.g., 26), or an electrostatic lens (e.g., 30) can be evaluated or monitored via time-resolved readings of applied voltage magnitude associated with each component. Deviations of the voltage measurements obtained from these components from nominal conditions, or from an alignment voltage range, can signal that the beam passing through the injector system is misaligned.

For example, embodiments described herein can determine that a beam propagating through the beam injector is misaligned when at least one current measurement obtained from at least one magnetic element of the beam injector deviates from an alignment current range. Alternatively or in addition, embodiments herein can determine that a beam propagating through the beam injector is misaligned when at least one voltage measurement obtained from at least one biased component of the beam injector deviates from an alignment voltage range.

Embodiments described herein can further enable redundancy in detection of beam misalignment in a beam injector system through the use of one or more beam position monitors (not shown in FIG. 2) along the beam injector system. Embodiments described herein can further enable redundancy in detection of beam misalignment in a beam injector system through the use of one or more scraper members (not shown in FIG. 2) along the beam injector system. Each scraper member can be configured as a plate, panel, or strut that extends into close proximity with the beam. The plate, panel, or strut can be configured to surround the beam, e.g., can have an aperture through which the beam passes. Annular members are also suitable. Deviation of the beam from the optimum axis can cause the beam, or the beam halo, to impact the scraper member.

Detection of beam misalignment in a beam injector system can be determined based on the existence of a signal (e.g., current measurement) obtained from a magnetic element of the beam injector violating a condition indicative of beam misalignment (e.g., deviating from a threshold of nominal conditions, or deviating from an alignment current range). Detection of beam misalignment in a beam injector system can be determined based on the existence of a signal (e.g., voltage measurement) obtained from a biased component of the beam injector violating a condition indicative of beam misalignment (e.g., deviating from a threshold of nominal conditions, or deviating from an alignment voltage range). Detection of beam misalignment in a beam injector system can be determined based on a signal received from a beam position monitor indicating that the beam is off axis. Detection of beam misalignment in a beam injector system can be determined based on measured signals from one or more scraper members. Detection of beam misalignment in a beam injector system can further be determined based on a combination of two or more of the foregoing conditions and, in some embodiments, a determination of beam misalignment can only be reached if two or more misalignment conditions are satisfied.

A control system (described with respect to FIG. 7) can be configured to adjust beam parameters or discontinue beam propagation or system operation based on any of the above determinations or detections.

Figure 3:
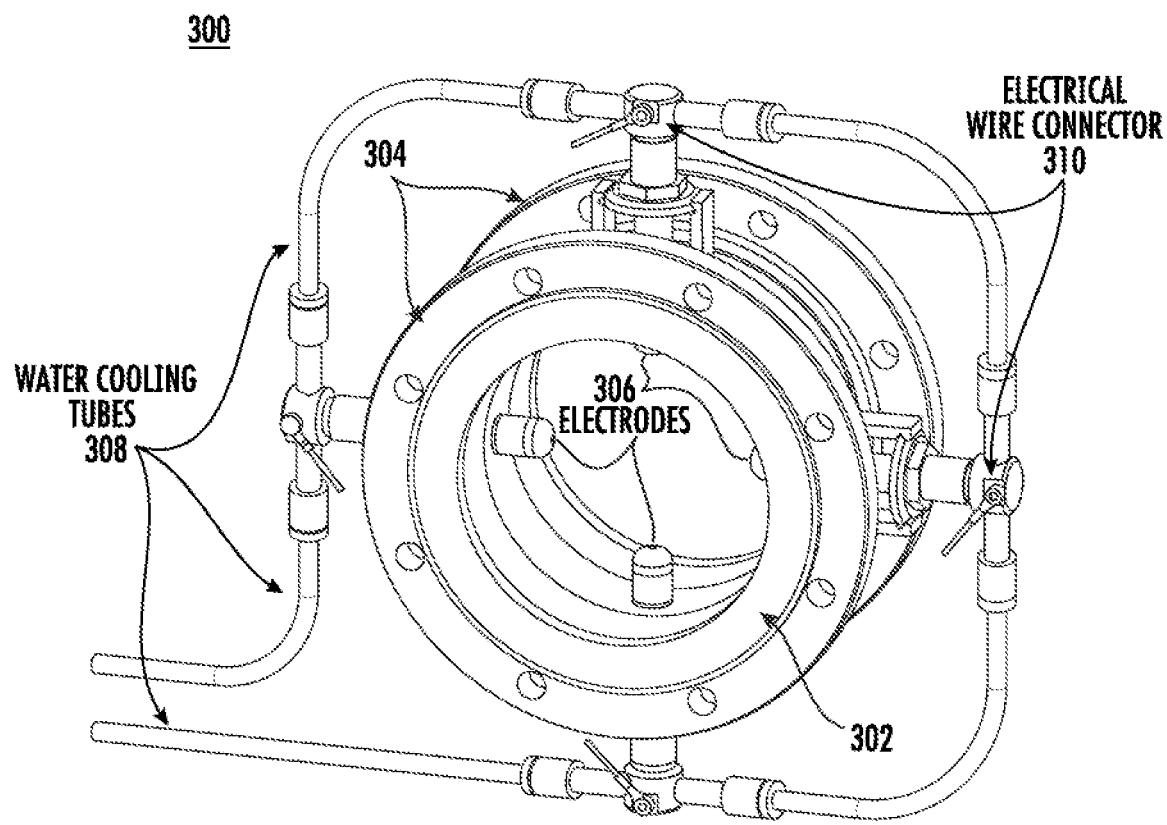
FIG. 3 is a perspective view of an example embodiment of a beam position monitor (BPM) of the ion beam injector system shown in FIG. 2.

Turning to FIG. 3, an example beam position monitor (BPM) (e.g., or fast beam position monitor) 300 includes a cylindrical wall 302 extending between a pair of flanges 304 adapted to mount the beam position monitor (BPM) 300 along the beam line (e.g., low energy beamline (LEBL) 14 (e.g., pre-accelerator or injector system 20), accelerator 16, high energy beamline (HEBL) 100). In examples where the beam position monitor (BPM) 300 is mounted along the low energy beamline (LEBL), the beam position monitor (BPM) 300 can be mounted between the pre-accelerator tube 26 and pumping chamber 28. The beam position monitor (BPM) 300 may be electrically couplable by way of one or more electrical wire connectors (310). The operation of the beam position monitor (BPM) 300 can be based on collection of the beam halo current by electrodes 306 protruding from the wall 302 and extending into the interior of the beam line. In example embodiments, electrodes 306 can be cooled by way of one or more cooling devices. In example embodiments, the one or more cooling devices can include water cooling devices (e.g., water cooling tubes 308).

In FIG. 3, the beam position monitor (BPM) 300 is shown to include four electrodes 306, although embodiments are not limited to four electrodes (e.g., any number of electrodes can be employed within the scope of the present disclosure). The electrodes 306 are preferably shaped as cylinders and made of one or more of tantalum (Ta) or tungsten (W) to increase resistance to the heat flux. The electrodes 306 can also be made of composite materials and different shapes that are able to withstand the thermal load generated by the beam. The insertion length (e.g., electrode extension distance into the interior of the beam line) of an electrode 306 can be adjusted separately for each electrode 306 (e.g., using a control system, not shown in FIG. 3), allowing a user to adapt the beam position monitor (BPM) 300 for beams of arbitrary dimensions. The electrodes 306 are intended to be exposed to the beam halo current, therefore the collected power flux is anticipated to be much lower. Moreover, the plasma formed near the region of the beam-residual gas interaction expands to the beam outer boundary forming an additional signal for the beam position monitor (BPM) 300.

Electrodes 306 can be galvanically isolated from the BPM wall 302 and biased using an external power supply. Biasing relative to the BPM wall 302 a) can reduce contribution of secondary electron emission (SEE) current to the signal and b) can increase the beam halo current collected from the beam generated plasma.

While the beam system is operating and a beam is being extracted from a source (e.g., 12) and propagated through components (e.g., 20 (14), 16, 18, 100) of an example beam system g., 10), the beam position monitor (BPM) 300 enables a control system to actively monitor the beam position. Each electrode 306 can have associated with it a current threshold (e.g., a signal threshold). When collected current (e.g., or signal) by a given electrode exceeds its current threshold, the beam can be deemed to have deflected too far toward that electrode and, as such, be off axis. The beam position monitor (300) can provide an indication that current collected by the electrode has exceeded its current threshold to the control system, and the control system can adjust parameters of one or more components of the entire beam system (e.g., 10) to move the beam back on axis. Examples of adjustable parameters can include inputs provided to beam steering magnets such that positions of the beam steering magnets are altered to move the beam back onto the desired axis. In this manner, the beam position monitor (BPM) 300 along with the control system continuously/repeatedly and in real time provide feedback to the beam steering magnets and/or other components of the beam system.

In embodiments, a current threshold associated with a given electrode can be different from a current threshold associated with another electrode of the beam position monitor (300). Further, a given electrode can have associated with it multiple current thresholds for more granular detection of beam position. That is, multiple current thresholds can be used with the electrodes of the beam position monitor (300). Detection of movement of the beam off axis in a direction between electrodes can be based on multiple current thresholds associated with adjacent electrodes.

For example, a pair of adjacent electrodes can both register an increase in signal level (e.g., current collected), however the increase in signal level can exceed a second, lower current threshold associated with each electrode of the pair of adjacent electrodes. In such an example, the signal level exceeding the second, lower current threshold associated with each electrode of the pair of adjacent electrodes can indicate that the beam is in an off-axis direction between the electrodes.

Accordingly, the control system can adjust the beam steering magnets based on an indication that the signal level exceeds a single threshold for a single electrode of the beam position monitor (BPM) 300, or based on an indication that the signal level exceeds two lower thresholds for adjacent electrodes.

Moreover, the control system can monitor the magnitudes of signal on each of the electrodes and extrapolate a degree of beam deflection in a particular direction based on the magnitudes of the signal (e.g., independent of or in combination with one or more current thresholds associated with the electrodes). The control system can then adjust the beam steering magnets, or other parameters, based on the extrapolated degree(s) of beam deflection in order to compensate for the beam deflection and bring the beam back to its desired axis. In such examples, the control system can continuously and in real-time adjust beam line parameters, such as positions of the beam steering magnets, based on a minimum amount of detected deflection (e.g., a deflection threshold).

Figure 4A:
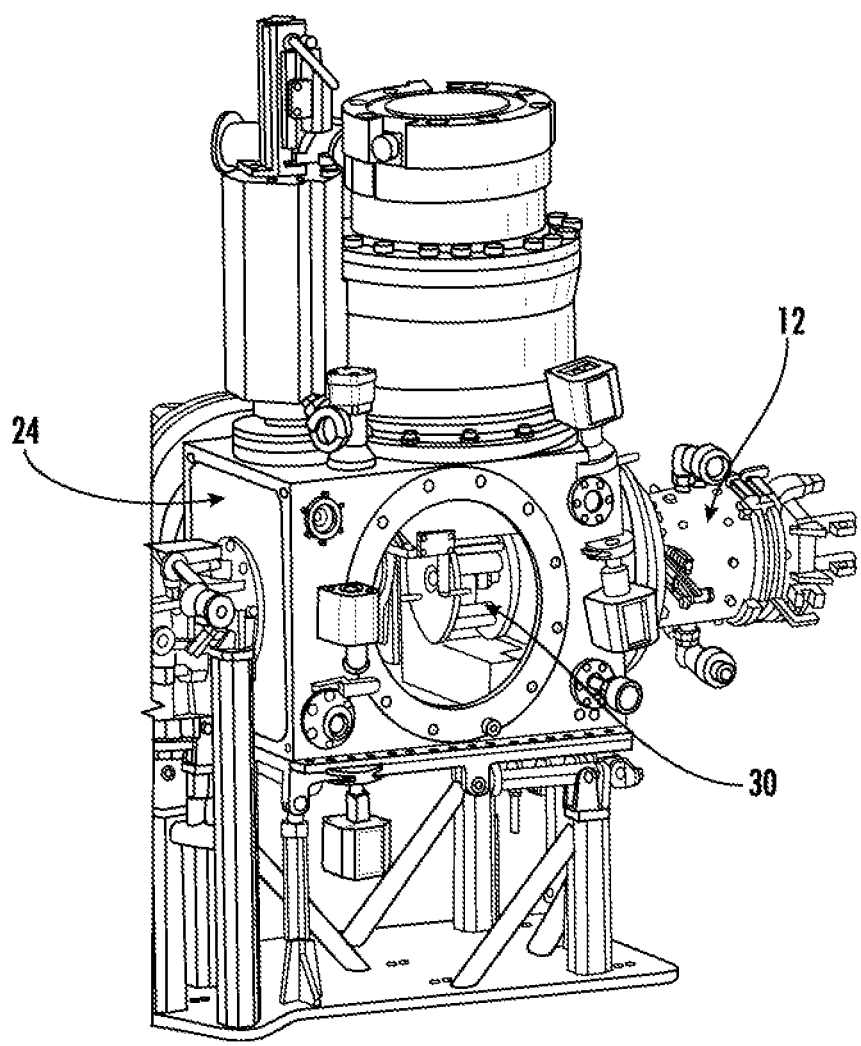
FIG. 4A is a perspective view of the ion source and the ion source vacuum box shown in FIG. 2.
Figure 4B:
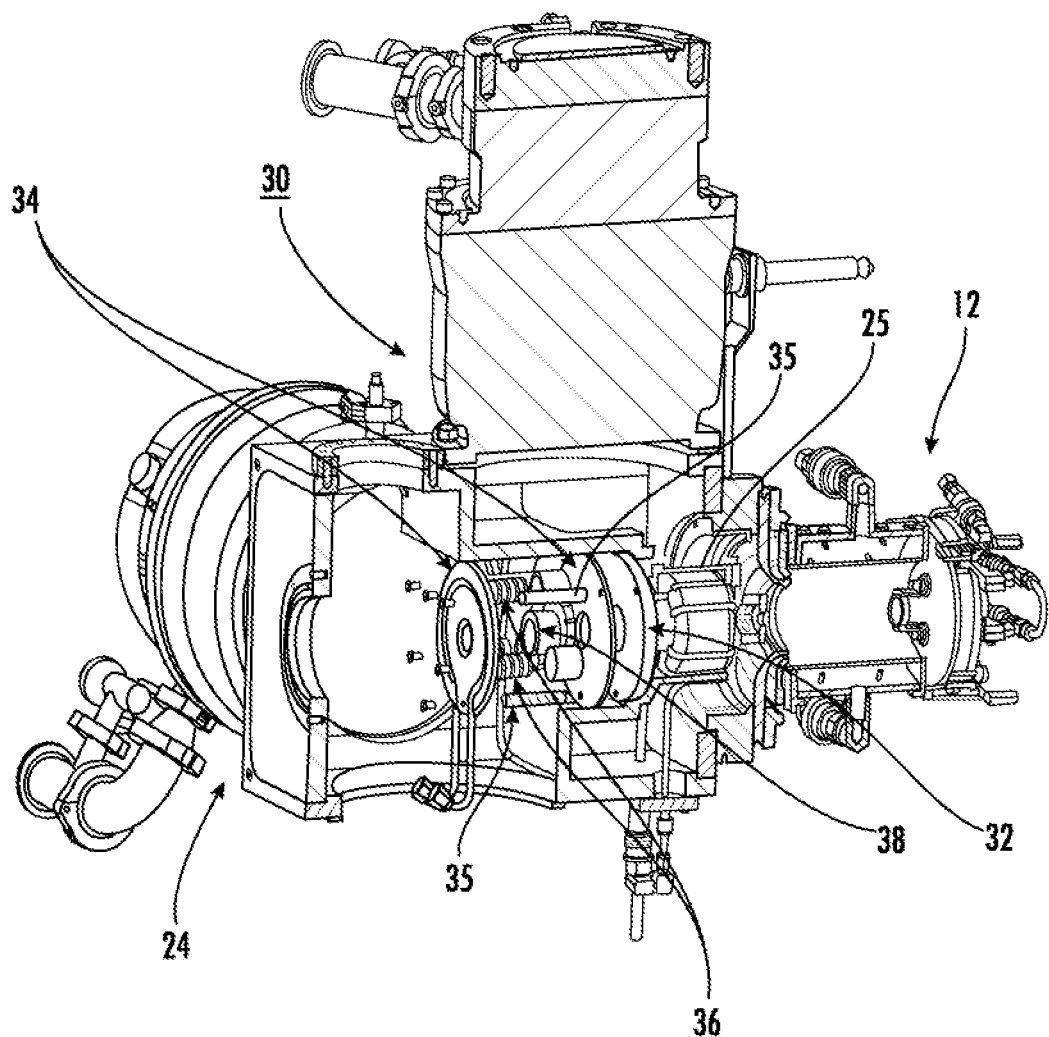
FIG. 4B is an exploded perspective view depicting an example embodiment of the einzel lens shown in FIG. 4A.

Turning to FIG. 4A, the ion source vacuum box 24 of the ion beam injector 20 (14) can include an einzel lens 30 positioned therein. As shown in detail in FIG. 4B, the einzel lens 30, which can be mounted downstream of a ground lens 25 of the ion source 12 within the vacuum box 24, includes a mounting plate 32, two grounded electrodes 34 mounted to the mounting plate 32 and coupled to one of another in spaced relation with mounting rods 35, and a powered (biased) electrode 38 positioned between the two grounded electrodes 34. The electrodes 34 and 38 are configured as cylindrical apertures and assembled to have an axial axis coinciding with the beam path. The powered electrode 38 is supported by isolators (or insulators) 36 extending between the grounded electrodes or apertures 34.

The standoff isolators 36 can have a geometric design configured to inhibit development of electron avalanches and to suppress streamer formation and propagation which can result in a flashover formation. The geometric design of standoff isolators 36 can partially screen an external electric field on the insulator surface which drives the electron avalanche and effectively increases the path length. In addition, the materials of insulators/isolators 36 tend to diminish sputtering effects, loss of negative ions on surfaces, volume contamination, and formation of a conductive coating on the insulator or isolator surfaces leading to a decrease of electrical strength.

Functionally, action of the einzel lens 30 on the beam of charged particles advancing from the ion source 12 is akin to the action of optical focusing lens on a beam of light. Namely, the einzel lens 30 is focusing the incoming diverging beam into a spot at the focal plane. However, here the electric fields formed between the pairs of the powered electrode 38 and the two grounded electrodes 34 determine the focusing strength of the einzel lens (focal length distance). By mounting the einzel lens 30 downstream of the ion source ground lens 25, it diminishes beam free space transportation where the beam is subjected to divergence due to intrinsic space charge. The dimensions of the axisymmetric or substantially axisymmetric design of the einzel lens 30 are optimized to avoid direct interaction of extracted ions with exposed surfaces of the einzel lens 30.

Figure 5:
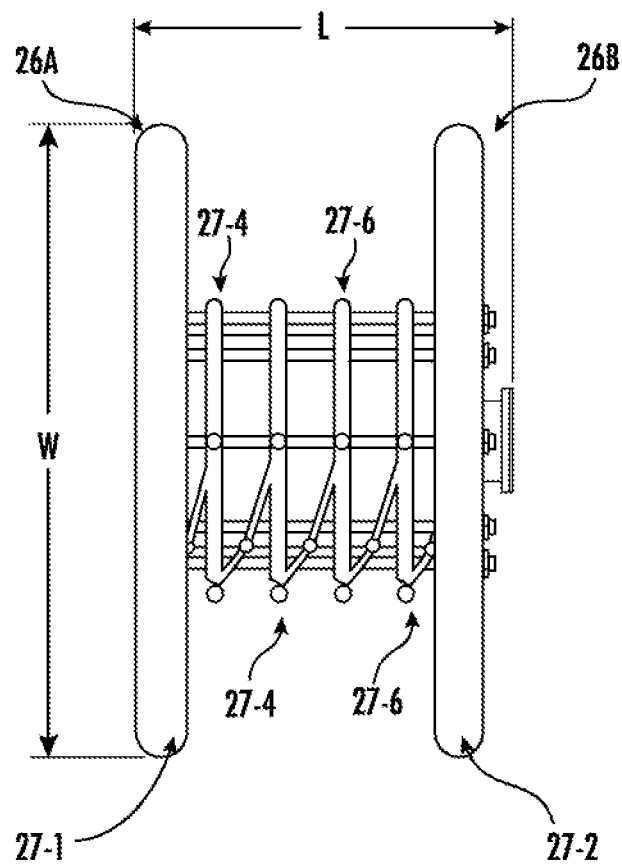
FIG. 5 illustrates an example pre-accelerator tube for use with embodiments of the present disclosure.

FIG. 5 illustrates an example pre-accelerator tube 26 for use with embodiments of the present disclosure. An example pre-accelerator tube 26 can be cylindrical in shape and includes a first pre-accelerator tube end 26A and a second pre-accelerator tube end 26B. In embodiments, the first pre-accelerator tube end 26A includes a fixture (e.g., a terminal or electrode) protruding outward from an inner cylindrical structure of the pre-accelerator tube. In embodiments, the second pre-accelerator tube end 26B includes a fixture (e.g., a terminal or electrode) protruding outward from an inner cylindrical structure of the pre-accelerator tube. That is, the fixtures protruding outward from the inner cylindrical structure of the pre-accelerator tube are cylindrical in shape but can have a larger diameter than that of the inner cylindrical structure. In embodiments, pre-accelerator tube 26 includes multiple pre-accelerator tube terminals 27-1, 27-2, 27-3, 27-4, 27-5, 27-6 evenly spaced from the first pre-accelerator tube end 26A to the second pre-accelerator tube end 26B. The first pre-accelerator tube end 26A can be referred to in some implementations as a proximal pre-accelerator tube end 26A in relation to the second pre-accelerator tube 26B being a distal pre-accelerator tube end 26B. Each pair of adjacent pre-accelerator tube terminals (e.g., pre-accelerator tube terminals 27-1, 27-2, 27-3, 27-4, 27-5, 27-6) can have one or more resistors connected therebetween, and the resistors can have the same (preferred) or different resistance values. In embodiments, a first terminal 27-1 at the first pre-accelerator tube end 26A is electrically couplable with a first power supply, while a second terminal 27-2 at the second pre-accelerator tube end 26B is electrically couplable with ground. Accordingly, voltage can be distributed evenly across the pre-accelerator tube 26.

Figure 6:
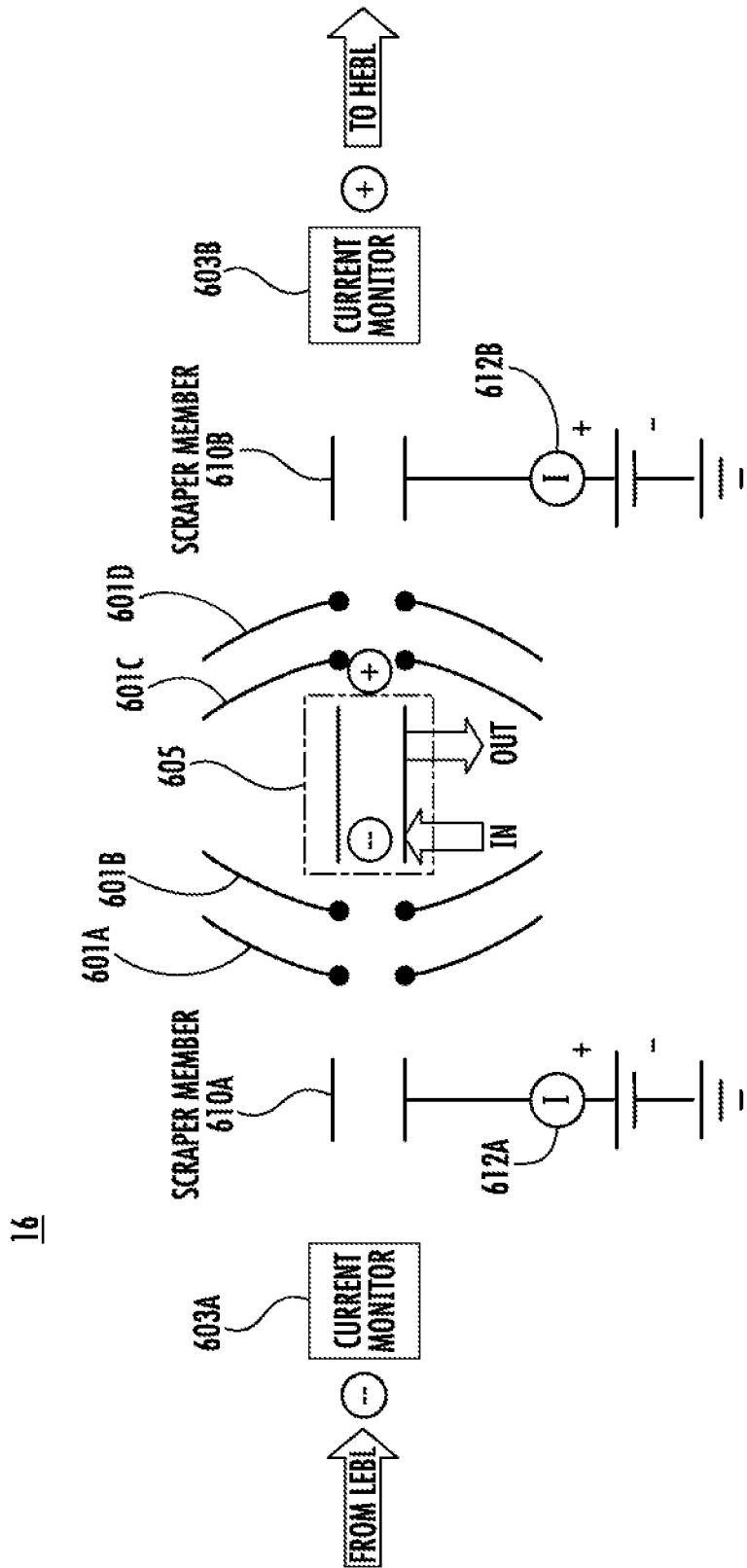
FIG. 6 illustrates example operations of an example embodiment of the present disclosure.

FIG. 6 illustrates example operation associated with example embodiments of the present disclosure. Turning to detection of beam misalignment in an accelerator system, the accelerator system (e.g., 16) is where charged particles of the beam are accelerated to a desired energy. This embodiment of the accelerator system (e.g., 16) relies on a stripping of two electrons from each negative ion during a charge-exchange process to produce the beam of energy doubled from the applied voltage. Optimized for beam efficient transport, acceleration, and electron stripping, an example accelerator system can have conditions (strong E-fields, space limitations, high potentials) preventing the use of direct beam diagnostics. Such conditions can make beam monitoring inside the accelerator system (e.g., 16) a very difficult task.

Due to a high voltage applied to accelerating electrodes (e.g., 601A, 601B, 601C, 601D), the accelerator system (e.g., 16) can be characterized by a presence of dark current even without beam transport. In contrast to other particle accelerators, a tandem accelerator relies on stripping of charges to achieve tandem-type acceleration of particles. Therefore, vacuum conditions inside the tandem promote beam interaction with a charge exchange medium (e.g., Argon) resulting in development of dark current. This process can result in incomplete voltage breakdown event affecting the beam energy. While the tandem accelerator can still continue operation, the accelerated beam can no longer be safe for downstream beamline components and should be discontinued.

Embodiments herein enable multiple points of detection of beam losses inside the accelerator system (e.g., 16) such that beam-wall interaction is detected and limited to a sub-millisecond duration. One or more of multiple points of detection can be considered by the control system in order to determine whether a beam is misaligned (e.g., beam-wall interaction is present), to determine whether to send signals to one or more beam line components to adjust beam parameters, or to determine whether to send signals to one or more beam line components to discontinue beam or beam system operation.

Shown in FIG. 6, total beam current upstream and downstream the accelerator system 16 can be monitored using beam current monitors 603A, 603B (e.g., non-invasive diagnostics), respectively. A difference in the measured currents obtained by way of beam current monitors 603A and 603B can indicate beam losses experienced inside the accelerator system 16.

For example, a comparison of input beam current and output beam current can represent beam losses in the accelerator system.

$$I_{losses}^1 = I_{CM}^{LEBL} - I_{SM}^{LEBL} - I_{CM}^{HEBL} + I_{SM}^{HEBL},$$

where CM stands for current monitor (e.g., 603A, 603B), SM stands for scraper member (e.g., 610A, 610B), LEBL stands for low energy beamline, HEBL stands for high energy beamline. For example, $I_{CM}^{LEBL}$ can be the current measured at the current monitor positioned between the LEBL and the accelerator system (e.g., in this example, 603A), while $I_{CM}^{HEBL}$ can be the current measured at the current monitor positioned between the HEBL and the accelerator system (e.g., in this example, 603B). Continuing with the example, $I_{SM}^{LEBL}$ can be the current measured at the scraper member positioned between the LEBL and the accelerator system (e.g., in this example, 610A), while a $I_{SM}^{HEBL}$ can be the current measured at the scraper member positioned between the LEBL and the accelerator system (e.g., in this example, 610B). Current monitors or detectors 612A, 612B can be used to measure current at the scraper members 610A, 610B, respectively. The charge exchange process (stripping) efficiency can be assumed at 100% for simplicity of description, however, it can be accounted for in the $I_{CM}^{HEBL}$ term. A threshold or alignment range can be associated with $I_{losses}^1$ such that deviation within a given range can be considered tolerable. Deviation outside of a given threshold or alignment range can be considered a signal of beam misalignment.

A first scraper member 610A can be positioned at an entrance or input aperture of the accelerator system 16, and a second scraper member 610B can be positioned at an exit or output aperture of the accelerator system 16. In example embodiments, scraper members 610A and 610B can be configured to cut off or reduce the beam halo current and serve as limiters. The first scraper member 610A positioned at the entrance or input aperture can be configured to absorb a significant portion of the beam current. Scraper members 610A and 610B are preferably configured to measure an incoming flux of charged particles (e.g., current). Both members 610A, 610B can be biased to suppress secondary emissions and configured to signal or provide to the control system indication of the collected current.

Power supply output voltage and current of the accelerator system 16 can also be measured and monitored as part of beam misalignment detection. Measuring the accelerator (e.g., tandem) current which includes stripped electrons:

$$I_{tandem} = (I_{CM}^{LEBL} - I_{SM}^{LEBL}) + (I_{CM}^{HEBL} - I_{SM}^{HEBL}) = I_{in} + I_{out}.$$

If a parasitic discharge is developed inside the accelerator system, the above equality will not be fulfilled. Therefore, a condition $I_{tandem} \geq \alpha(I_{in} + I_{out})$ can be designated as an interlock trigger (e.g., signal of beam misalignment) to discontinue the beam because incomplete breakdown of the accelerator system is likely to occur. Here, $\alpha$ can be adjusted or configured based on the accelerator system power supply characteristics, beam current, beam energy, and the like, to ensure safe beam transport. Alternatively, the beam losses can be expressed as:

$$I_{losses}^2 = 2I_{in} - I_{tandem} \text{ or } I_{losses}^2 = I_{tandem} - 2I_{out},$$

which enables a redundant estimate of beam losses via accelerator current measurements.

A flow rate and temperature of charge exchange device coolant can also be measured at inlet and outlet within the accelerator system 16. During prolonged operation of the accelerator system 16, beam losses inside the charge exchange (CEX) device 605 having or including the charge exchange medium can be also estimated via an example heat balance equation:

$$\frac{dQ}{dt} = P_{beam} - P_{cool} = 0,$$

where $P_{beam} = I_{losses}^3 \cdot E_{beam}$ and $P_{cool} = q \cdot c_p \cdot \rho \cdot dT$, thus $I_{losses}^3 = C \dfrac{q \cdot dT}{E_{beam}}, C = c_p \cdot \rho.$ Here q is a flow rate of coolant (oil), $c_p$ and $\rho$ are oil specific heat and density, dT is a temperature difference of coolant between inlet (e.g., IN) and outlet (e.g., OUT), and $E_{beam}$ is an energy of particles striking the CEX device 605. These indirectly measured beam losses on the charge exchange device 605 can be used to set up interlocks (e.g., misalignment signals or thresholds, or thresholds for discontinuing beam propagation) as $I_{losses}^3 \geq \delta I_{beam}$, $I_{losses}^3 \leq \beta I_{losses}^1$ and $I_{losses}^3 \geq \gamma I_{losses}^2$ where $\delta$, $\beta$ and $\gamma$ are adjustable parameters. The CEX device 605 is configured in FIG. 6 as a tubular member into which the charge exchange medium is introduced and held temporarily before escaping to the vacuum environment of the accelerator. The CEX device 605 can be configured in other ways, such as any structure with an interior volume sufficient to at least temporarily hold or direct the flow of the charge exchange medium.

Figure 7:
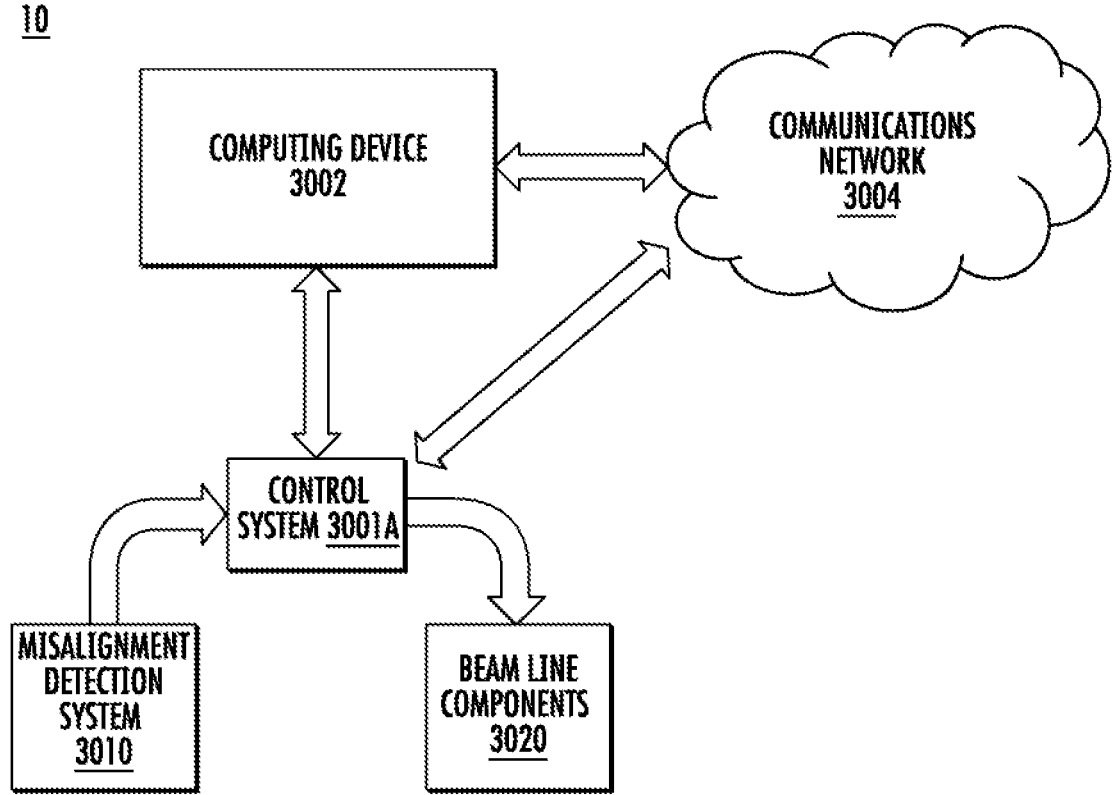
FIG. 7 illustrates a block diagram of a system within which embodiments of the present disclosure can operate.

FIG. 7 is a block diagram depicting an example embodiment of a control system with which embodiments of the present disclosure can operate. For example, the illustrated example system includes beam system 10 and one or more computing devices 3002. In embodiments, beam system 10 can be part of an example neutron beam system (e.g., system 10 above). In such embodiments, the beam system 10 can employ one or more control systems 3001A with which one or more computing devices 3002 can communicate in order to interact with the systems and components of the beam system 10 (e.g., neutron beam system 10). Each of these devices and/or systems are configured to communicate directly with one another or via a local network, such as network 3004.

Computing devices 3002 can be embodied by various user devices, systems, computing apparatuses, and the like. For example, a first computing device 3002 can be a desktop computer associated with a particular user, while another computing device 3002 can be a laptop computer associated with a particular user, and yet another computing device 3002 can be a mobile device (e.g., a tablet or smart device). Each of the computing devices 3002 can be configured to communicate with the beam system 10, for example through a user interface accessible via the computing device. For example, a user can execute a desktop application on the computing device 3002, which is configured to communicate with the beam system 10.

By using a computing device 3002 to communicate with beam system 10, a user can provide operating parameters for the beam system 10 (e.g., operating voltages, and the like) according to embodiments described herein.

Control system 3001A can be configured to receive measurements, signals, or other data from components of the beam system 10. For example, control system 3001A can receive signals from an example misalignment detection system 3010 indicative of misalignment of a beam passing through the beam system 10. The control system 3001A, depending on the degree or signal of misalignment, can provide adjustments to inputs of one or more beam line components 3020 to alter the position of the beam according to the methods described herein. The control system 3001A can also, or alternatively, cause the beam system to stop or discontinue propagation of the beam, e.g., by not biasing an extraction electrode on the ion source. The control system 3001A can also output an indication of beam misalignment, or the degree of beam misalignment, to the computing device 3002 (and the user). Similarly, the control system 3001A can provide information collected from any of the components of the beam system 10, including the misalignment detection system 3010, to the computing device 3002 either directly or via communications network 3004.

Communications network 3004 can include any wired or wireless communication network including, for example, a wired or wireless local area network (LAN), personal area network (PAN), metropolitan area network (MAN), wide area network (WAN), or the like, as well as any hardware, software and/or firmware required to implement it (such as, e.g., network routers, etc.). For example, communications network 3004 can include an 802.11, 802.16, 802.20, and/or WiMax network. Further, the communications network 3004 can include a public network, such as the Internet, a private network, such as an intranet, or combinations thereof, and can utilize a variety of networking protocols now available or later developed including, but not limited to TCP/IP based networking protocols.

Figure 8:
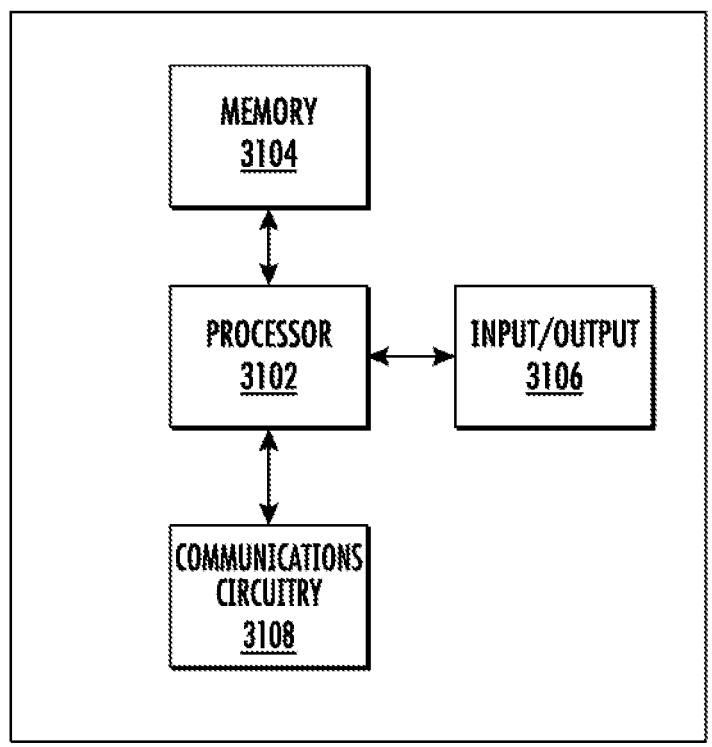
FIG. 8 illustrates an example computing apparatus that can be specially configured in accordance with embodiments of the present disclosure.

The computing device 3002, misalignment detection system 3010, and control system 3001A can be embodied by one or more computing systems, such as apparatus 3100 shown in FIG. 8. As illustrated in FIG. 8, the apparatus 3100 can include a processor 3102, a memory 3104, an input and/or output circuitry 3106, and communications device or circuitry 3108. It should also be understood that certain of these components 3102-3108 can include similar hardware. For example, two components can both leverage use of the same processor, network interface, storage medium, or the like to perform their associated functions, such that duplicate hardware is not required for each device. The use of the terms "device" and/or "circuitry" as used herein with respect to components of the apparatus therefore can encompass particular hardware configured with software to perform the functions associated with that particular device, as described herein.

The terms "device" and/or "circuitry" should be understood broadly to include hardware, in some embodiments, device and/or circuitry can also include software for configuring the hardware. For example, in some embodiments, device and/or circuitry can include processing circuitry, storage media, network interfaces, input/output devices, and the like. In some embodiments, other elements of the apparatus 3100 can provide or supplement the functionality of particular device(s). For example, the processor 3102 can provide processing functionality, the memory 3104 can provide storage functionality, the communications device or circuitry 3108 can provide network interface functionality, and the like.

In some embodiments, the processor 3102 (and/or co-processor or any other processing circuitry assisting or otherwise associated with the processor) can be in communication with the memory 3104 via a bus for passing information among components of the apparatus. The memory 3104 can be non-transitory and can include, for example, one or more volatile and/or non-volatile memories. In other words, for example, the memory can be an electronic storage device (e.g., a computer readable storage medium.) The memory 3104 can be configured to store information, data, content, applications, instructions, or the like, for enabling the apparatus to carry out various functions in accordance with example embodiments of the present disclosure.

The processor 3102 can be embodied in a number of different ways and can, for example, include one or more processing devices configured to perform independently. Additionally or alternatively, the processor can include one or more processors configured in tandem via a bus to enable independent execution of instructions, pipelining, and/or multithreading. The use of the terms "processing device"

and/or "processing circuitry" can be understood to include a single core processor, a multi-core processor, multiple processors internal to the apparatus, and/or remote or "cloud" processors.

In an example embodiment, the processor 3102 can be configured to execute instructions stored in the memory 3104 or otherwise accessible to the processor. Alternatively or additionally, the processor can be configured to execute hard-coded functionality. As such, whether configured by hardware or software methods, or by a combination of hardware with software, the processor can represent an entity (e.g., physically embodied in circuitry) capable of performing operations according to an embodiment of the present disclosure while configured accordingly. Alternatively, as another example, when the processor is embodied as an executor of software instructions, the instructions can specifically configure the processor to perform the algorithms and/or operations described herein when the instructions are executed.

In some embodiments, the apparatus 3100 can include input/output device 3106 that can, in turn, be in communication with processor 3102 to provide output to the user and, in some embodiments, to receive input from the user. The input/output device 3106 can include a user interface and can include a device display, such as a user device display, that can include a web user interface, a mobile application, a client device, or the like. In some embodiments, the input/output device 3106 can also include a keyboard, a mouse, a joystick, a touch screen, touch areas, soft keys, a microphone, a speaker, or other input/output mechanisms. The processor and/or user interface circuitry including the processor can be configured to control one or more functions of one or more user interface elements through computer program instructions (e.g., software and/or firmware) stored on a memory accessible to the processor (e.g., memory 3104, and/or the like).

The communications device or circuitry 3108 can be any means such as a device or circuitry embodied in either hardware or a combination of hardware and software that is configured to receive and/or transmit data from/to a network and/or any other device or circuitry in communication with the apparatus 3100. In this regard, the communications device or circuitry 3108 can include, for example, a network interface for enabling communications with a wired or wireless communication network. For example, the communications device or circuitry 3108 can include one or more network interface cards, antennas, buses, switches, routers, modems, and supporting hardware and/or software, or any other device suitable for enabling communications via a network. Additionally or alternatively, the communication interface can include the circuitry for interacting with the antenna(s) to cause transmission of signals via the antenna(s) or to handle receipt of signals received via the antenna(s). These signals can be transmitted by the apparatus 3100 using any of a number of wireless personal area network (PAN) technologies, such as current and future Bluetooth standards (including Bluetooth and Bluetooth Low Energy (BLE)), infrared wireless (e.g., IrDA), FREC, ultra-wideband (UWB), induction wireless transmission, or the like. In addition, it should be understood that these signals can be transmitted using Wi-Fi, Near Field Communications (NFC), Worldwide Interoperability for Microwave Access (WiMAX), or other proximity-based communications protocols.

Any such computer program instructions and/or other type of code can be loaded onto a computer, processor, or other programmable apparatus' circuitry to produce a machine, such that the computer, processor, or other programmable circuitry that executes the code on the machine creates the means for implementing various functions, including those described herein.

As described above, embodiments of the present disclosure can be configured as systems, methods, mobile devices, backend network devices, and the like. Accordingly, embodiments can include various structures including entirely of hardware or any combination of software and hardware. Furthermore, embodiments can take the form of a computer program product on at least one non-transitory computer-readable storage medium having computer-readable program instructions (e.g., computer software) embodied in the storage medium. Any suitable computer-readable storage medium can be utilized including non-transitory hard disks, CD-ROMs, flash memory, optical storage devices, or magnetic storage devices.

Processing circuitry for use with embodiments of the present disclosure can include one or more processors, microprocessors, controllers, and/or microcontrollers, each of which can be a discrete chip or distributed amongst (and a portion of) a number of different chips. Processing circuitry for use with embodiments of the present disclosure can include a digital signal processor, which can be implemented in hardware and/or software of the processing circuitry for use with embodiments of the present disclosure. Processing circuitry for use with embodiments of the present disclosure can be communicatively coupled with the other components of the figures herein. Processing circuitry for use with embodiments of the present disclosure can execute software instructions stored on memory that cause the processing circuitry to take a host of different actions and control the other components in figures herein.

Memory for use with embodiments of the present disclosure can be shared by one or more of the various functional units, or can be distributed amongst two or more of them (e.g., as separate memories present within different chips). Memory can also be a separate chip of its own. Memory can be non-transitory, and can be volatile (e.g., RAM, etc.) and/or non-volatile memory (e.g., ROM, flash memory, F-RAM, etc.).

Computer program instructions for carrying out operations in accordance with the described subject matter can be written in any combination of one or more programming languages, including an object oriented programming language such as Java, JavaScript, Smalltalk, C++, C#, Transact-SQL, XML, PHP or the like and conventional procedural programming languages, such as the "C" programming language or similar programming languages.

Various aspects of the present subject matter are set forth below, in review of, and/or in supplementation to, the embodiments described thus far, with the emphasis here being on the interrelation and interchangeability of the following embodiments. In other words, an emphasis is on the fact that each feature of the embodiments can be combined with each and every other feature unless explicitly stated otherwise or logically implausible.

In some embodiments, a method of detecting beam misalignment in a beam injector includes obtaining at least one current measurement from at least one magnetic element of the beam injector and at least one voltage measurement from at least one biased component of the beam injector. In some of these embodiments, the method further includes determining that a beam propagating through the beam injector is misaligned when one or more of the at least one current measurement obtained from at least one magnetic element of the beam injector deviates from an alignment current range or at least one voltage measurement obtained from at least one biased component of the beam injector deviates from an alignment voltage range.

In some of these embodiments, the beam injector includes a beam position monitor. In some of these embodiments, the method further includes determining that the beam propagating through the beam injector is misaligned when an output signal from the beam position monitor indicates a signal at one or more individual electrodes of the beam position monitor violates a condition. In some of these embodiments, the method further includes determining that the beam propagating through the beam injector is misaligned when an output signal from the beam position monitor indicates a first magnitude of current at one or more individual electrodes of the beam position monitor exceeds or is below a first current threshold.

In some of these embodiments, the beam injector includes one or more scraper members. In some of these embodiments, the method further includes obtaining one or more measurements from at least one scraper member of the one or more scraper members and determining that the beam propagating through the beam injector is misaligned when the one or more measurements obtained from at least one scraper member deviate from an alignment threshold.

In some of these embodiments, the at least one magnetic element includes a beam steering magnet or a solenoid.

In some of these embodiments, the at least one biased component includes an ion source, a pre-accelerator tube, or an electrostatic lens.

In some of these embodiments, the beam injector is injecting a beam to an accelerator system.

In some of these embodiments, the method further includes deactivating the beam propagating through the beam injector upon determining that the beam is misaligned.

In some of these embodiments, the method further includes signaling beam misalignment to a control system or computing device upon determining that the beam is misaligned.

In some embodiments, a system for detecting beam misalignment in a beam injector includes a beam injector and a control system including at least one processor and at least one memory storing instructions that, with the at least one processor, configure the control system to obtain at least one current measurement from at least one magnetic element of the beam injector and at least one voltage measurement from at least one biased component of the beam injector. In some of these embodiments, the at least one memory stores instructions that, with the at least one processor, further configure the control system to determine that a beam propagating through the beam injector is misaligned when one or more of the at least one current measurement obtained from at least one magnetic element of the beam injector deviates from an alignment current range or at least one voltage measurement obtained from at least one biased component of the beam injector deviates from an alignment voltage range In some of these embodiments, the beam injector includes a beam position monitor.

In some of these embodiments, the at least one memory stores instructions that, with the at least one processor, further configure the control system to determine that the beam propagating through the beam injector is misaligned when an output signal from the beam position monitor indicates a signal at one or more individual electrodes of the beam position monitor violates a condition.

In some of these embodiments, the at least one memory stores instructions that, with the at least one processor, further configure the control system to determine that the beam propagating through the beam injector is misaligned when an output signal from the beam position monitor indicates a first magnitude of current at one or more individual electrodes of the beam position monitor exceeds or is below a first current threshold.

In some of these embodiments, the beam injector includes one or more scraper members.

In some of these embodiments, the at least one memory stores instructions that, with the at least one processor, further configure the control system to obtain one or more measurements from at least one scraper member of the one or more scraper members, and determine that the beam propagating through the beam injector is misaligned when the one or more measurements obtained from at least one scraper member deviate from an alignment threshold.

In some of these embodiments, the at least one magnetic element includes a beam steering magnet or a solenoid.

In some of these embodiments, the at least one biased component includes an ion source, a pre-accelerator tube, or an electrostatic lens.

In some of these embodiments, the beam injector is configured to inject a beam to an accelerator system.

In some of these embodiments, the at least one memory stores instructions that, with the at least one processor, further configure the control system to deactivate the beam propagating through the beam injector upon determining that the beam is misaligned.

In some of these embodiments, the at least one memory stores instructions that, with the at least one processor, further configure the control system to signal beam misalignment to a computing device upon determining that the beam is misaligned.

In some embodiments, a method of detecting beam misalignment in an accelerator system includes obtaining an input beam current at an input aperture of the accelerator system, obtaining an output beam current at an output aperture of the accelerator system, and determining that a beam propagating through the accelerator system is misaligned when a difference between the output beam current and the input beam current indicates beam losses exceeding a beam loss threshold.

In some of these embodiments, the input beam current is determined from a first current monitor measurement and a first scraper member measurement.

In some of these embodiments, the output beam current is determined from a second current monitor measurement and a second scraper member measurement.

In some of these embodiments, the method further includes signaling to a control system or computing device that the beam is misaligned.

In some of these embodiments, the method further includes signaling to a control system or computing device the difference between the output beam current and the input beam current.

In some of these embodiments, the method further includes discontinuing beam propagation upon determining that the beam is misaligned.

In some embodiments, a method of detecting beam misalignment in an accelerator system includes obtaining an input beam current at an input aperture of the accelerator system, obtaining an output beam current at an output aperture of the accelerator system, and determining that a beam propagating through the accelerator system is misaligned when a difference between a current of the accelerator system and a sum of the output beam current and the input beam current is greater than zero.

In some of these embodiments, the input beam current is composed of a first current monitor measurement and a first scraper member measurement.

In some of these embodiments, the output beam current is composed of a second current monitor measurement and a second scraper member measurement.

In some of these embodiments, the method further includes signaling to a control system or computing device that the beam is misaligned.

In some of these embodiments, the method further includes signaling to a control system or computing device the difference between the output beam current and the input beam current.

In some of these embodiments, the method further includes discontinuing beam propagation upon determining that the beam is misaligned.

In some embodiments, a method of detecting beam misalignment in an accelerator system includes obtaining a flow rate of coolant of a target exchange cooling device of the accelerator system, an energy of particles striking a charge exchange device of the accelerator system, and a temperature difference of coolant between an inlet and an outlet of the charge exchange cooling device. In some of these embodiments, the method further includes determining that a beam propagating through the accelerator system is misaligned based when beam losses calculated based on the flow rate, energy, and temperature difference exceed a beam loss threshold.

In some of these embodiments, the method further includes signaling to a control system or computing device that the beam is misaligned.

In some of these embodiments, the method further includes signaling to a control system or computing device the flow rate, energy, and temperature difference.

In some of these embodiments, the method further includes discontinuing beam propagation upon determining that the beam is misaligned.

In some embodiments, a method of detecting beam misalignment in an accelerator system includes obtaining an input beam current at an input aperture of the accelerator system, obtaining an output beam current at an output aperture of the accelerator system, or obtaining a flow rate of coolant of a charge exchange cooling device of the accelerator system, an energy of particles striking a charge exchange device of the accelerator system, and a temperature difference of coolant between an inlet and an outlet of the charge exchange cooling device. In some of these embodiments, the method further includes one or more of determining that a beam propagating through the accelerator system is misaligned when a difference between the output beam current and the input beam current indicates beam losses exceeding a beam loss threshold, or determining that a beam propagating through the accelerator system is misaligned when a difference between a current of the accelerator system and a sum of the output beam current and the input beam current is greater than zero, or determining that a beam propagating through the accelerator system is misaligned based when beam losses calculated based on the flow rate, energy, and temperature difference exceed a beam loss threshold.

In some embodiments, a system for detecting beam misalignment in an accelerator system includes an accelerator system and a control system including at least one processor and at least one memory storing instructions that, with the at least one processor, configure the control system to perform methods according to any of the foregoing embodiments.

In some of these embodiments, the system further includes a first current monitor positioned at an input aperture of the accelerator system and a second current monitor positioned at an output aperture of the accelerator system. In some of these embodiments, the system further includes a first scraper member positioned at an input aperture of the accelerator system and a second scraper member positioned at an output aperture of the accelerator system.

In some of these embodiments, the system further includes a charge exchange device and a charge exchange cooling device.

In some embodiments, a beam system includes a system for detecting beam misalignment in a beam injector according to any of the foregoing embodiments. In some of these embodiments, the beam system further includes a system for detecting beam misalignment in an accelerator system according to any of the foregoing embodiments.

In some embodiments, a method for detecting beam misalignment in a beam system includes one or more of detecting beam misalignment in a beam injector of the beam system according to a method of any of the foregoing embodiments. In some of these embodiments, the method further includes detecting beam misalignment in an accelerator system of the beam system according to a method of any of the foregoing embodiments.

It should be noted that all features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. It is explicitly acknowledged that express recitation of every possible combination and substitution is overly burdensome, especially given that the permissibility of each and every such combination and substitution will be readily recognized by those of ordinary skill in the art.

To the extent the embodiments disclosed herein include or operate in association with memory, storage, and/or computer readable media, then that memory, storage, and/or computer readable media are non-transitory. Accordingly, to the extent that memory, storage, and/or computer readable media are covered by one or more claims, then that memory, storage, and/or computer readable media is only non-transitory.

As used herein and in the appended claims, the singular forms "a," "an," and "the" include plural referents unless the context clearly dictates otherwise.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, steps, or elements of the embodiments can be recited in or added to the claims, as well as negative limitations that define the inventive scope of the claims by features, functions, steps, or elements that are not within that scope.

What is claimed is:

1. A method of detecting beam misalignment in a beam injector, the method comprising:
   obtaining at least one current measurement from at least one magnetic element of the beam injector and at least one voltage measurement from at least one biased component of the beam injector; and
   determining that a beam propagating through the beam injector is misaligned when one or more of the at least one current measurement obtained from at least one magnetic element of the beam injector deviates from an alignment current range or at least one voltage measurement obtained from at least one biased component of the beam injector deviates from an alignment voltage range.

2. The method of claim 1, wherein the beam injector comprises a beam position monitor.

3. The method of claim 2, further comprising:
   determining that the beam propagating through the beam injector is misaligned when an output signal from the beam position monitor indicates a signal at one or more individual electrodes of the beam position monitor violates a condition.

4. The method of claim 2, further comprising:
   determining that the beam propagating through the beam injector is misaligned when an output signal from the beam position monitor indicates a first magnitude of current at one or more individual electrodes of the beam position monitor exceeds or is below a first current threshold.

5. The method of claim 1, wherein the beam injector comprises one or more scraper members.

6. The method of claim 5, further comprising:
   obtaining one or more measurements from at least one scraper member of the one or more scraper members; and
   determining that the beam propagating through the beam injector is misaligned when the one or more measurements obtained from at least one scraper member deviate from an alignment threshold.

7. The method of claim 1, wherein the at least one magnetic element comprises a beam steering magnet or a solenoid.

8. The method of claim 1, wherein the at least one biased component comprises an ion source, a pre-accelerator tube, or an electrostatic lens.

9. The method of claim 1, wherein the beam injector is injecting a beam to an accelerator system.

10. The method of claim 1, further comprising:
    deactivating the beam propagating through the beam injector upon determining that the beam is misaligned.

11. The method of claim 1, further comprising:
    signaling beam misalignment to a control system or computing device upon determining that the beam is misaligned.

12. A system for detecting beam misalignment in a beam injector, the system comprising:
    a beam injector; and
    a control system comprising at least one processor and at least one memory storing instructions that, with the at least one processor, configure the control system to:
    obtain at least one current measurement from at least one magnetic element of the beam injector and at least one voltage measurement from at least one biased component of the beam injector; and
    determine that a beam propagating through the beam injector is misaligned when one or more of the at least one current measurement obtained from at least one magnetic element of the beam injector deviates from an alignment current range or at least one voltage measurement obtained from at least one biased component of the beam injector deviates from an alignment voltage range.

13. The system of claim 12, wherein the beam injector comprises a beam position monitor.

14. The system of claim 13, wherein the at least one memory stores instructions that, with the at least one processor, further configure the control system to:
    determine that the beam propagating through the beam injector is misaligned when an output signal from the beam position monitor indicates a signal at one or more individual electrodes of the beam position monitor violates a condition.

15. The system of claim 13, wherein the at least one memory stores instructions that, with the at least one processor, further configure the control system to:
    determine that the beam propagating through the beam injector is misaligned when an output signal from the beam position monitor indicates a first magnitude of current at one or more individual electrodes of the beam position monitor exceeds or is below a first current threshold.

16. The system of claim 12, wherein the beam injector comprises one or more scraper members.

17. The system of claim 16, wherein the at least one memory stores instructions that, with the at least one processor, further configure the control system to:
    obtain one or more measurements from at least one scraper member of the one or more scraper members; and
    determine that the beam propagating through the beam injector is misaligned when the one or more measurements obtained from at least one scraper member deviate from an alignment threshold.

18. The system of claim 12, wherein the at least one magnetic element comprises a beam steering magnet or a solenoid.

19. The system of claim 12, wherein the at least one biased component comprises an ion source, a pre-accelerator tube, or an electrostatic lens.

20. The system of claim 12, wherein the beam injector is configured to inject a beam to an accelerator system.

21. The system of claim 12, wherein the at least one memory stores instructions that, with the at least one processor, further configure the control system to:
    deactivate the beam propagating through the beam injector upon determining that the beam is misaligned.

22. The system of claim 12, wherein the at least one memory stores instructions that, with the at least one processor, further configure the control system to:
    signal beam misalignment to a computing device upon determining that the beam is misaligned.

* * * * *